(12) United States Patent
Weigel et al.

(10) Patent No.: US 8,652,621 B2
(45) Date of Patent: Feb. 18, 2014

(54) ITEM WITH AT LEAST ONE THERMOPROGRAMMABLE SWITCHING SECTION FOR APPLICATIONS IN CONTACT WITH MATERIALS HAVING HIGH HEAT TRANSFER COEFFICIENTS

(75) Inventors: Thomas Weigel, Michendorf (DE); Andreas Lendlein, Berlin (DE); Karola Lützow, Berlin (DE); Frank Klein, Berlin (DE); Samy Madbouly, Cairo (EG)

(73) Assignee: Helmholtz-Zentrum Geesthacht Zentrum fur Material und Kustenforschung GmbH, Geesthacht (DE)

( * ) Notice: Subject to any disclaimer, the term of this patent is extended or adjusted under 35 U.S.C. 154(b) by 384 days.

(21) Appl. No.: 13/126,822

(22) PCT Filed: Oct. 30, 2009

(86) PCT No.: PCT/EP2009/064367
§ 371 (c)(1),
(2), (4) Date: Jul. 19, 2011

(87) PCT Pub. No.: WO2010/049521
PCT Pub. Date: May 6, 2010

(65) Prior Publication Data
US 2011/0305889 A1 Dec. 15, 2011

(30) Foreign Application Priority Data

Oct. 31, 2008 (DE) .................. 10 2008 043 357
Mar. 5, 2009 (DE) .................. 10 2009 001 356

(51) Int. Cl.
*B32B 7/02* (2006.01)
*B32B 3/26* (2006.01)
*B05D 1/02* (2006.01)

(52) U.S. Cl.
USPC ............... 428/212; 428/304.4; 427/427.4; 521/144

(58) Field of Classification Search
None
See application file for complete search history.

(56) References Cited

U.S. PATENT DOCUMENTS

| | | | |
|---|---|---|---|
| 6,967,051 B1 * | 11/2005 | Augustynowicz et al. | ..... 428/68 |
| 2004/0219130 A1 | 11/2004 | Ito et al. | |
| 2005/0212630 A1 | 9/2005 | Buckley et al. | |
| 2007/0173800 A1 | 7/2007 | Sanders et al. | |
| 2008/0004692 A1 | 1/2008 | Henson et al. | |

FOREIGN PATENT DOCUMENTS

| | | |
|---|---|---|
| DE | 102007061342 | 6/2009 |
| WO | WO 02/12409 | 2/2002 |
| WO | WO 2004/056156 | 7/2004 |

OTHER PUBLICATIONS

International Search Report dated Mar. 2, 2010.
Gall et al., Carbon fiber reinforced shape memory polymer composites, *Journal of Intelligent Material Systems and Structures*, vol. 11, pp. 877-886 (2000).

(Continued)

*Primary Examiner* — David Sample
*Assistant Examiner* — Nicole T Gugliotta
(74) *Attorney, Agent, or Firm* — VLP Law Group LLP (57) ABSTRACT

The present invention provides an article with at least one switching segment. The switching segment comprises a shape-memory compound and an isolating region surrounding the shape memory compound. The present invention also provides a method of producing such an article.

20 Claims, 7 Drawing Sheets

(56) References Cited

OTHER PUBLICATIONS

Gotthard et al., Smart materials based on shape memory alloys: Examples from Europe, *Materials Science Forum*, vols. 327-328 (2000) pp. 83-90.

Gall et al., Shape memory polymer nanocomposites, *Acta Materialia*, 50 (2002) 5115-5126.

Li et al., Polyurethane/Conducting carbon black composites: structure, electric conductivity, strain recovery behavior, and their relationships, *Journal of Applied Polymer Science*, vol. 75, 68-77 (2000).

Monkman, G.J., Advances in shape memory polymer actuation, *Mechatronics*, 10 (2000) 489-498.

Liang et al., Investigation of Shape Memory Polymers and Their Hybrid Composites, *Journal of Intelligent Material Systems and Structures*, vol. 8 (1997).

\* cited by examiner

ITEM WITH AT LEAST ONE THERMOPROGRAMMABLE SWITCHING SECTION FOR APPLICATIONS IN CONTACT WITH MATERIALS HAVING HIGH HEAT TRANSFER COEFFICIENTS

PRIORITY CLAIM

This is a U.S. national stage of application No. PCT/EP2009/064367, filed on Oct. 30, 2009. Priority is claimed on the following applications: German Application No. 102008043357.8 filed on Oct. 31, 2008 and German Application No. 102009001356.3 filed on Mar. 5, 2009, the contents of which are incorporated here by reference.

BACKGROUND OF THE INVENTION

Shape memory plastics can have a permanent original shape stored in addition to a visible temporary shape. By activating an external stimulus, for example a temperature increase, the permanent shape can be almost completely recalled, i.e., the plastic "remembers" its original shape.

The material is thereby first transformed into its original, permanent shape by using conventional processing methods, such as extrusion, injection molding as well as also from a polymer solution. The plastic is then deformed and fixed in the desired temporary shape. This process is called programming. It includes either heating the sample above the switching temperature $T_{sw}$ and below the highest transition temperature $T_{perm}$, deforming the sample by forcing a shape and then cooling the sample while maintaining the forced shape. Alternatively, programming can also be performed by deformation at a low temperature below the switching temperature $T_{sw}$ ("cold stretching").

The permanent shape is now stored, while the temporary shape is actually present. The memory shape effect is activated by heating the plastic to a temperature higher than the switching temperature $T_{sw}$, with the material returning to the stored permanent shape due to its entropy elasticity.

If the transition from the temporary to the permanent shape is caused by a temperature change, then this is called a thermally induced shape memory effect. This thermally induced shape memory effect is in most situations realized by direct temperature action (application of heat). In addition, indirect heating is known. For example, it is known to incorporate nanoscale particles in a shape memory plastic, which to interact with an externally generated alternating electromagnetic field (EMF). In this way, a temperature rise in the shape memory polymer can be obtained "indirectly" by way of the embedded nanoparticles.

The ability of these nanoparticles to realize heating through excitation via an EMF has already been implemented in several applications. The electric eddy currents induced in electrically conducting particles in the EMF generate heat. This principle was not only used in technological applications, for example as innovative gluing technique for hardening adhesives (WO 2004/056156 A, WO 2002/012409 A), but nanoparticies have already been used in bio-medical applications for destroying metastases of tumors by short local overheating of the body tissue (US 2004219130 A).

The use of additives in shape memory polymers has until now mostly been the subject off studies that mainly focused on changes in the physical properties, for example the conductivity, the structure or the restoring forces during the switching process (Li F. et al.: Polyurethane/Conducting Carbon Black Composites: Structure, Electric Conductivity, Strain Recovery Behavior, and Their Relationships. Journal of Applied Polymer Science 75 (1), 68-77 (2000)). The type of the additives that were until now added in these studies to the shape memory polymers, range from carbon fibers (Gall K. et al.: Carbon fiber reinforced shape memory polymer composites. Journal of Intelligent Material Systems and Structures 11 (11), 877-886 (2001); Liang C. et al.: Investigation of shape memory polymers and their hybrid composites. Journal of Intelligent Material Systems and Structures 8 (4), 380-386 (1997)) and SiC (Gall K. et al.: Shape memory polymer nanocomposites. Acta Materialia 50, 5115-5126 (2002)) to metals (Gotthardt R. et al.: Smart materials based on shape memory alloys (SMAs): examples from Europe. Materials Science Forum 327-328 (Shape Memory Materials), 83-90 (2000); Monkmann G. J.: Advances in Shape Memory Polymer Actuation. Mechatronics 10, 489-498 (2000)). For example, the addition of carbon fibers to shape memory polymers is mainly intended to increase the strength or stiffness. Typical effects caused by the addition of metals or metal alloys as particle additives to the shape memory polymers are discussed in Monkmann (see above) based on comparative studies with a particle-free shape memory polymers and in Gotthardt R. in relation to damping oscillations in skis.

The company CTD (Lafayette, Colo., USA), which designed their product "Tembo" for application in space, describes the use of thermal conductors embedded in shape memory polymers. The shape memory function was here intended to be used for heating a hinge to unfold solar panels, which are still folded up when transported into space.

Iron oxide embedded in a silicate layer which heats up when an alternating magnetic field is applied has recently been offered by the company "Advanced Nanomaterials".

A new approach is admixture of ferromagnetic or metallic particles to a shape memory polymer (US 20050212630 A). The particles are hereby used as "antenna" for activating the shape memory effect through an external stimulus. DE 10 2007 061 342.5 discloses corresponding mixtures of shape memory polymers with suitable particles, as well as a method for their production and thermal programming and switching. The content disclosed in DE 10 2007 061 342.5 is fully incorporated into the present application. The external stimulus is here an alternating electromagnetic field which generates heat in the ferromagnetic or metallic particles, causing a temperature increase of the shape memory polymer and hence activation of the shape memory effect. The magnitude of the attainable temperature increase depends on many parameters. These parameters include, on one hand, parameters determined by the EMF, in particular frequency and field strength of the alternating field. On the other hand, the maximally attainable material temperature for a predetermined field depends on the composition of the mixture, which contains a shape memory polymer and suitable nanoparticles, in particular on the size, the type, the quantity and the thermal conductivity of the nanoparticles. It has also been observed that the surface-to-volume ratio (O/V) also has an affect on the attainable material temperature due to the associated heat transfer to the surroundings. Therefore, shape memory bodies with a relatively small O/V can reach higher material temperatures in the EMF in than those with a large surface.

However, optimization of the aforementioned parameter is not always sufficient to attain the required switching temperature in the shape memory body. In the medical field, when for example a shape memory body is used as a stitching material in the human body, frequency and field strength of the EMF cannot be freely selected for the purpose of coupling higher energies into the shape memory body, because the body would otherwise be damaged. The concentration of the nanoparticles can be increased only in a limited way while substantially maintaining the mechanical properties of the shape memory body. Lastly, the surface-to-volume ratio also has application-related limits.

It is therefore an object of the present invention to provide a shape memory body which can be switched in an EMF, whose stored shape can be recalled even in an environment composed of materials with high thermal transfer coefficients.

SUMMARY OF THE INVENTION

The object is solved by providing an article with at least one switching segment wherein the at least one switching segment includes
a) a shape-memory compound comprising at least one thermo-programmable shape memory polymer and particles embedded therein, which particles are suitable to heat up in an alternating electromagnetic field, wherein the shape memory compound has a thermal transfer coefficient $h_{schalt}$;
b) an isolating region surrounding the shape memory compound a) and having a thermal transfer coefficient $h_{iso}$;
wherein $h_{iso} < h_{schalt}$.

The switching segment has preferably a smooth and/or fluid-impermeable surface, which prevents a fluid and/or a gas from entering the isolating region.

Important for the operation of the switching segment is that the shape memory compound is returned to its original permanent shape when a switching temperature $T_{sw}$ of the at least one thermo-programmable shape memory polymer in the shape memory compound is exceeded. The required temperature is often difficult to attain in an environment which has a greater thermal transfer coefficient than the shape memory polymer of the switching segment. The solution presented in the present invention includes an isolating region which surrounds the active shape memory compound of a switching segment much like an isolating layer. This isolating region has a thermal transfer coefficient $h_{iso}$, which is smaller than the thermal transfer coefficient $h_{schalt}$ of the shape memory compound of the switching segment. In this way, the active region of the switching segment, where a temperature increase needs to be attained, independent of the surroundings in which the shape memory compound is located, is now surrounded by a region which has an advantageous heat transfer coefficient. The active region of a switching segment is then insulated from its environment. Thermal energy, which is supplied to a shape memory compound of a switching segment by an alternating external EMF, is then not so quickly carried away, so that a higher temperature can be attained in the shape memory compound, and a critical switching temperature $T_{sw}$ of the at least one thermo-programmable shape memory polymer can then also more easily be exceeded.

The article according to the invention has at least one switching segment. The article according to the invention hereby includes any object, provided this object has at least one switching segment.

The term switching segment refers to a region of the article which includes a shape memory compound and an isolating region. The switching segment has the purpose that the shape of the switching segment and therefore optionally the shape of the article can be changed by activating a switching operation in one region of the switching segment. For the purpose of the present invention, the term "switching segment" refers particularly to a region of an article that has a shape memory, is thermo-programmable and can be switched by an alternating external electromagnetic field, i.e., can be transformed from a temporary shape into a permanent shape.

To this end, the switching segment includes a shape memory compound. The term shape memory compound refers hereby to a composition which includes at least one thermo-programmable shape memory polymer and particles incorporated therein, which are able to heat up in an alternating electromagnetic field. In addition, a shape memory compound may include additional materials; in particular, a shape memory compound may include one or more identical or different additional shape memory polymers which need not all be thermo-programmable. The shape memory compound has a thermal transfer coefficient $h_{schalt}$.

The invention also includes those articles which are in their entirety composed of a shape memory compound which is partially or completely surrounded by the isolating region according to the invention.

The at least one thermo-programmable shape memory polymer is a conventional shape memory polymer or SMP with a thermally stimulated shape memory effect. In other words, it is capable to undergo at least one temperature-induced shape transition from a thermo-mechanically programmed temporary shape into a permanent shape. Such shape memory polymers are known to a person skilled in the art.

The at least one thermo-programmable shape memory polymer may, in particular, be a polymer network with a thermally inducible shape memory effect. The network can hereby be formed by covalent bonds or through physical interactions, for example electrostatic effects. In addition to cross-linking points, the polymer network includes at least one type of a switching segment which has a material-dependent transition temperature, such as a crystallization temperature or a glass transition temperature. Polymer networks with a shape memory effect are amply described in the literature. The present invention is fundamentally not limited to a specific material. For example, the polymer network may have a switching segment selected from the group consisting of polyester, in particular poly (☐-caprolactone); polyether, polyurethane, polyether urethane, polyamide, polyimide, polyether imide, polyacrylate, poly-methacrylate, polyvinyl, polystyrene, polyoxymethylene, poly (para-dioxanone) and others. The polymer network may also include two or more different switching segments from the present group or others. At least one switching segment is preferably selected to have a switching temperature in a range suitable for the respective application.

Optionally, the shape memory polymer may have hydrolytically cleavable groups, in particular ester-, amide-, anhydride-, carbonate-, ether-, orthoester groups or combinations thereof. Biodegradable materials can thereby be obtained, which have particular advantages in the biomedical field. Biodegradable shape memory polymers are also amply known from the literature. The present invention is not limited to specific representative compounds of this group.

Particles are incorporated in the at least one thermo-programmable shape memory polymer of a shape memory compound, wherein the particles are able to heat up in an alternating electromagnetic field. These can be nanoparticles or particles in a micrometer range. Microparticles are here defined by an average particle diameter in a range from 1 to 999 μm, and nanoparticles by an average particle diameter and arranged of 1 to 999 nm. This definition therefore includes that the particles can be introduced as a material having a powdery consistency. All those materials which are suitable to exhibit in an alternating magnetic field an interaction that causes heating of the particles can be considered for these particles. In particular, the particles may include metals, for example Ni, Fe and/or Co. Also suitable are alloys, in particular Ni—Si, Fe—Pt, Ni—Pd and/or Co—Pd. In addition, metal oxides can be used as magnetic material in the particles, in particular Ni—Zn—Fe—O, Ba—Co—Fe—O and/or Fe—O. Also suitable are magnetite or iron oxides, where the iron atoms are at least partially replaced by Ca, Ni, Mn, Zn, Mg, Cu, Cr, Cd and/or Ga. Also suitable are ferrites, in particular Ni—Zn-ferrites and/or Sr-ferrites. Mixtures of the aforementioned materials are also feasible. Preferably, those materials are used which can be homogeneously distributed in the polymer matrix, i.e., produce a very homogeneous mixture. However, if this property is absent, then the particles may have a coating of a material that improves intermixing with the shape memory polymer. The coating material may be in form of organic polymers. The nature, size, number and embedding process depends, for example, on the respective employed shape memory polymer, the switching temperature to be attained and the electromagnetic field (frequency and field strength) to be employed. Preferably, these are magnetic nanoparticles with an average particle size of <500 nm, particularly preferred of <100 nm. The particles may consist, for example, of a magnetic material or may have a layered structure, in which at least one layer has the property to heat up in an alternating electromagnetic field. A number of suppliers distribute suitable particles, and a person skilled in the art will have no difficulty to implement those particles with the present invention. It is particularly important that the nanoparticles can be functionally embedded in a shape memory polymer to be employed such that the nanoparticles can be heated by an alternating external electromagnetic field. Heating of the embedded nanoparticles then causes heating of the shape memory polymers surrounding the particles.

The at least one switching segment has a structure wherein a shape memory compound which is located—in cross-section—in the interior of the switching segment is enclosed by an isolating region located in relation thereto—also in cross-section—farther outward. The isolating region preferably surrounds the shape memory compound such that the shape memory compound of a switching segment of an article has no direct contact with a medium surrounding the article. The isolating region can here be directly deposited on the shape memory compound. However, additional layers may be present between the shape memory compound and the isolating region. The isolating region may also be contiguous with the shape memory compound and be manufactured together with the shape memory compound material. In particular, the shape memory compound may be completely enclosed by the isolating region. Preferably, no isolating region exists between the shape memory compound of a switching segment of an article and additional segments of the article connected to the switching segment.

The isolating region according to the invention is characterized in that it has a thermal transfer coefficient $h_{iso}$ which is smaller than the thermal transfer coefficient of the shape memory compound of a switching segment $h_{schalt}$, i.e., $h_{iso} < h_{schalt}$.

$h_{iso}$ can be calculated as follows:

$$h_{iso} = 2\lambda_{iso}/D_{iso+schalt} \ln(D_{schalt}/D_{iso+schalt})$$

wherein
$h_{iso}$ = thermal transfer coefficient of the isolating region
$\lambda_{iso}$ = specific thermal conductivity of the material of the isolating region
$D_{iso+schalt}$ = average diameter across the shape memory compound and the surrounding isolating region
$D_{schalt}$ = average diameter of the shape memory compound.

If the layer thickness of the isolating region is small compared to the average diameter of the shape memory compound, then $h_{iso}$ can be approximately computed as follows:

$$h_{iso} = \lambda_{iso}/x$$

wherein
$h_{iso}$ = thermal transfer coefficient of the isolating region
$\lambda_{iso}$ = specific thermal conductivity also material of the isolating region
x = average layer thickness of the isolating region.

In particular, the isolating region is constructed such that the ratio $h_{iso}/h_{schalt} \leq 0.9$, preferably $\leq 0.5$, particularly preferred $\leq 0.3$, and especially preferred $\leq 0.1$.

The isolating region may include one or more shape memory polymers which are also present in the shape memory compound of the switching segment. However, the isolating region may also include several materials which are not present in the shape memory compound. In particular, the isolating region can be constructed so as to have essentially no particles able to heat up in an alternating electromagnetic field. The isolating region may have a material or be made of a material having a specific thermal conductivity $\lambda_{iso}$ which is smaller than the specific thermal conductivity $\lambda_{schalt}$ of a material of the shape memory compound, preferably of the at least one thermo-programmable shape memory polymer of the shape memory compound.

The material with the smaller specific thermal conductivity $\lambda_{iso}$ of the isolating region may, in particular, be a gas. Preferably, a gas is used which is inert to other materials of the isolating region and/or of the shape memory compound. Particularly preferred, the gas is $CO_2$ or air or mixtures containing one of these gases in a concentration of $\geq 10$ mass-%. In particular, when the isolating region has a foam structure, parts of the cells or all cells of a foam structure may include such gas with a corresponding specific thermal conductivity.

To attain a particularly effective isolation of the shape memory compound of the switching segment, the isolating region may have a structure that is different from the structure of the shape memory compound. For example, the isolating region may be constructed from several identical or different layers or may have a porous structure. The porous structure may be essentially open-cell or closed-cell. If the isolating region has a porous structure, then a portion of or all cavities of the porous structure may be filled with a material that has a specific thermal transfer coefficient that is smaller than the specific thermal transfer coefficient of a thermo-programmable shape memory polymer of the shape memory compound of the switching segment. In particular, the isolating region may have a foam structure in parts or in total, in particular a predominantly closed-cell foam structure. The isolating region may have pores which are distributed across a cross-section of the isolating region along a pore size gradient, wherein the pores in an exterior region of the isolating region are on average smaller than the pores in an interior region of the isolating region. In a preferred embodiment, the isolating region has pores and/or foam cells with an average size of 5 to 50 µm.

Figure 3:
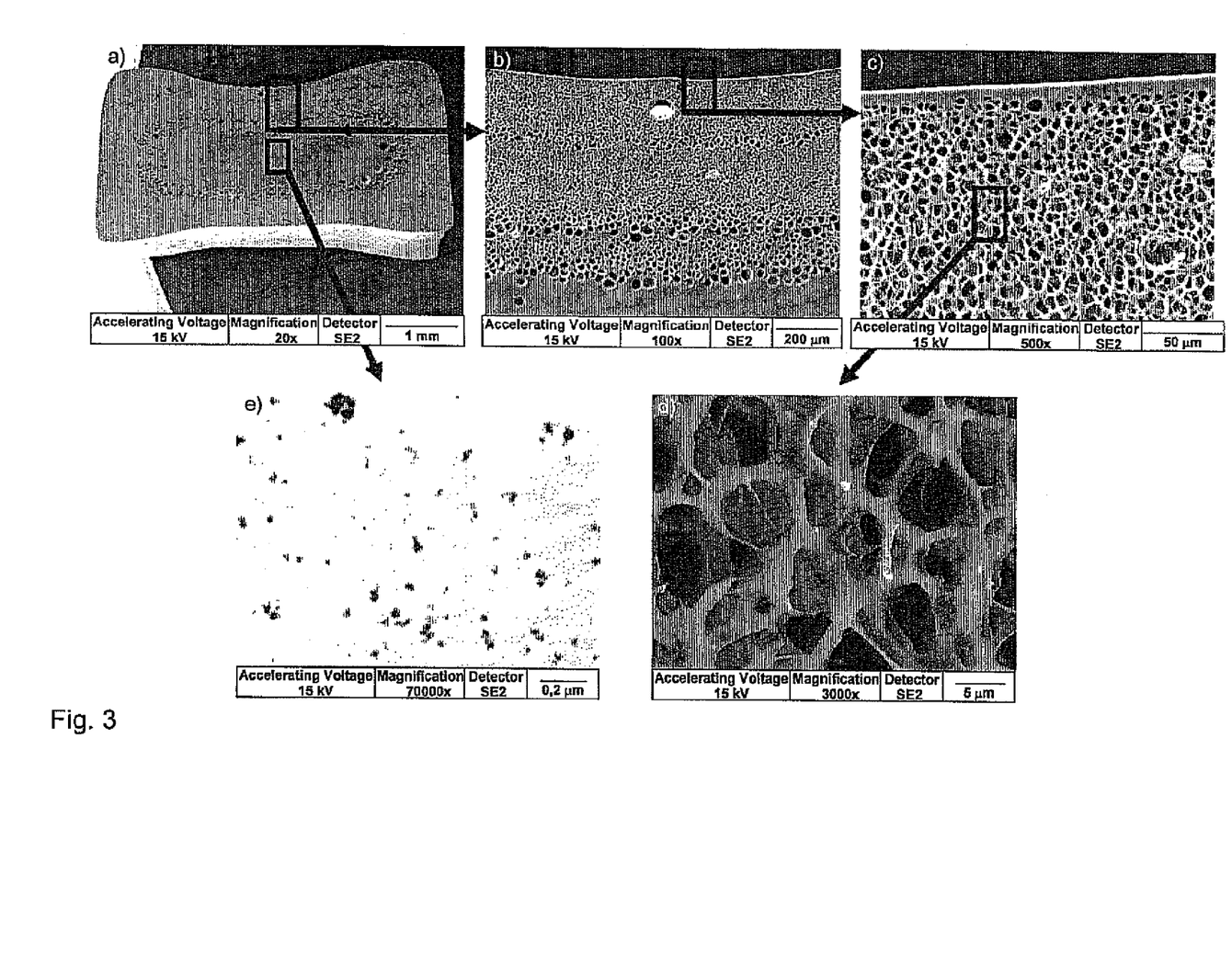

In particular, the switching segment, preferably the isolating region, may have a smooth exterior surface (see also FIGS. 3 a) to c)). This smooth surface of the switching segment and/or of the isolating region operates to ensure mechanical stability of the shape memory compound and to prevent other materials, for example liquids or gases, from entering the interior of the shape memory compound.

In particular, the isolating region may have an average layer thickness such that the shape memory compound is effectively isolated from the surroundings of switching segment. A skilled artisan will know in which environment the switching segment should be switched by an external electromagnetic field; a skilled artisan will also know which thermo-programmable shape memory polymer in the shape memory polymer of the switching segment is permeated with particles and should be switched, so that the skilled artisan can be readily determine the required average layer thickness of the isolating region for a predetermined EMF. If there limitations exist with respect to the EMF, then use of a weaker applied field may optionally be compensated by providing the isolating region with a certain thickness and/or by using particular materials with a particularly advantageous specific thermal conductivity.

In particular, the ratio of the average diameter of the isolating region and the shape memory compound ($D_{iso+schalt}$) to memory the average diameter of the shape memo compound ($D_{schalt}$) of the at least one switching segment ($D_{iso+schalt}/D_{schalt}$ may be selected in cross-section such that a switching temperature of the at least one thermo-programmable shape memory polymer of the shape memory compound can be attained in the shape memory compound through excitation with an alternating electromagnetic field, when the at least one switching segment is in an environment having a thermal transfer coefficient which is greater than the thermal transfer coefficient of the shape memory compound of the switching segment. The diameter ratio $D_{iso+schalt}/D_{schalt}$ may be selected such that the at least one switching segment attains the switching temperature in an aqueous environment and/or in an alternating electromagnetic field having a frequency of 245 to 265 kHz and a field strength of 10 to 16 kA/m.

The ratio of the average diameter of the isolating region and of the shape memory compound to the average diameter of the shape memory compound in cross-section of the at least one switching segment may be $D_{iso+schalt}/D_{shalt} \geq 1.01$, preferably $\geq 1.05$, particularly preferred $\geq 1.1$.

The isolating region has the function to reduce heat transfer from the article to the surroundings in the region of the switching segment, whereas in a shape memory compound of the switching segment, the body can be heated in the electromagnetic field by way of the embedded nanoparticles, without causing significant heat outflow into the surroundings of the article.

The switching segment can advantageously be hierarchically structured, i.e., in addition to the structure of the shape memory compound on the nano/micro level (hard domain and switching domain/nanoparticle), an additional organization in the μm/mm range is introduced, namely the structure in the isolating region and shape memory compound of a switching segment. This macro-structure is configured so as to achieve isolation between the surrounding medium and the shape memory compound of a switching segment of the article, thus reducing the heat transfer coefficient.

With the implementation of an isolating region or "sheath" which only permits small thermal transfer coefficients, the size of the temperature effect in the shape memory compound produced by an externally applied alternating EMF is now also sufficient in applications using fluids or areas with a high thermal transfer coefficient for achieving a shape memory effect.

The specially structured material can be implemented during the preparation of the shape memory compound as well as in a subsequent production process.

Figure 1:
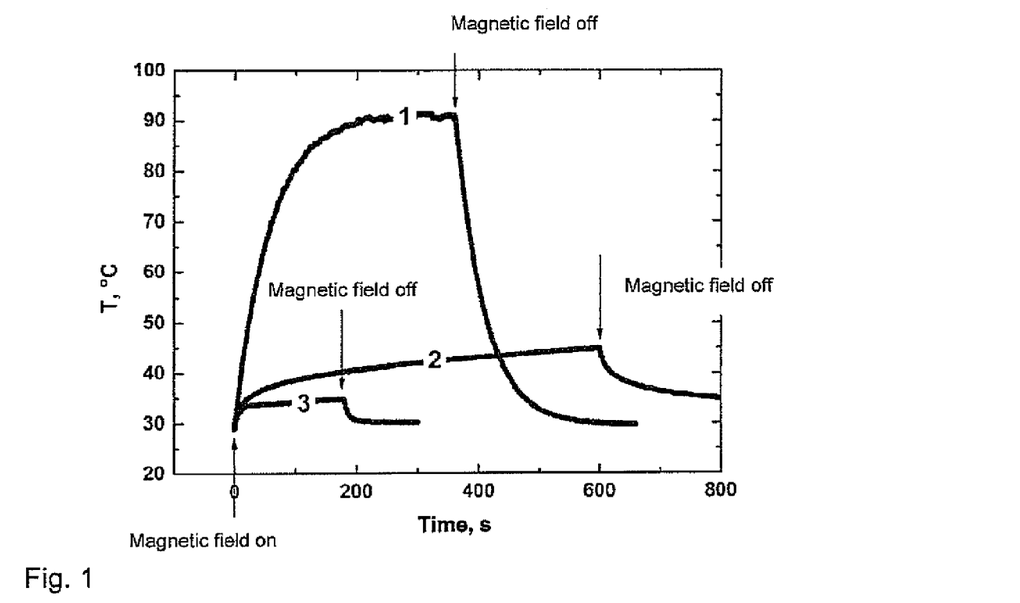
FIG. 1 Heating curves for shape memory compounds (18.1% nanoparticles in shape memory polymer) in different surroundings, 1—air, 2—10% gelatin in 0.5% NaCl solution, 3—distilled water.
Figure 2:
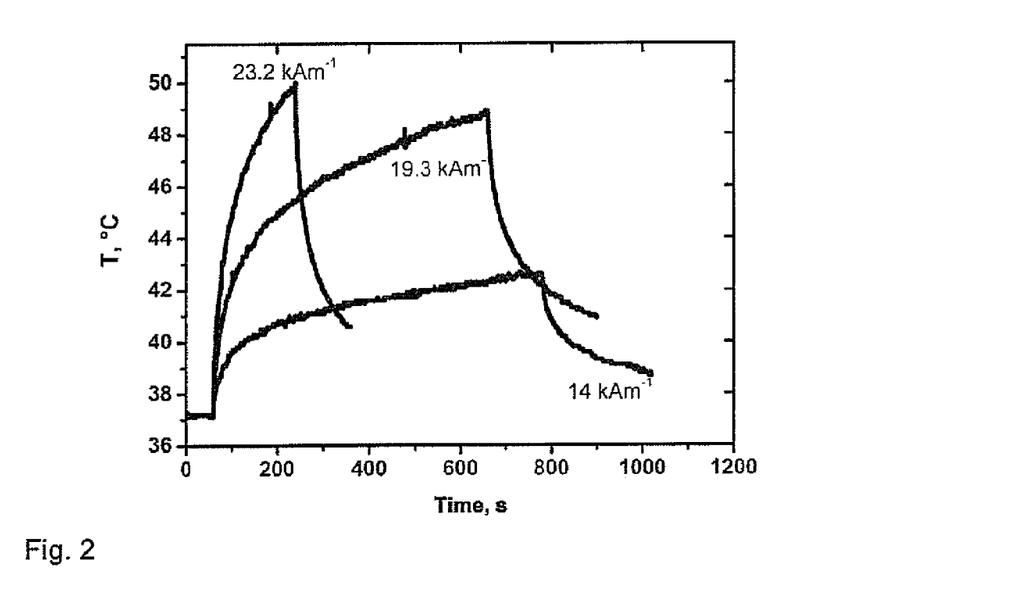
FIG. 2 Heating curves for shape memory compounds (14.4% nanoparticles in shape memory polymer with a surface/volume ratio of 8.3) in pork meat at a different magnetic field strengths.

For example, the invention makes use of the observation that the maximally attainable temperature rise of the material depends not only on the aforementioned parameters, but also strongly on the field of application, because the heat transfer to the adjacent materials also affect the maximally attainable temperature differences. The heat dissipation to the surroundings of the shape memory compound (expressed as thermal transfer coefficient) plays a particular role. At some point, equilibrium is reached between the thermal energy supplied via the EMF and the thermal energy dissipated by the nanoparticles to the surroundings, which results in a maximally attainable temperature. When a shape memory compound is in contact with materials having high thermal transfer coefficients, the attainable temperature difference is significantly less than if in contact with materials having small transfer coefficients, under otherwise comparable conditions. The supplied energy therefore is in the first case frequently insufficient to achieve temperatures that activate a thermal shape memory effect. This is emphasized in FIG. 1 and FIG. 2.

The advantages become particularly clear in the medical field when indirectly exciting nanoscale particles in shape memory compounds according to the invention with an externally operating EMF, with the associated temperature increase for activation of the shape memory effect. When the shape memory compound is used, for example, as stitching material in the human body, then high thermal transfer coefficients to the surrounding tissue inevitably result. The solution according to the invention is proposed for realizing the aforedescribed shape memory effect, for example, also under those conditions.

The invention also relates to articles according to the invention for applications where the article comes into contact with materials having a thermal transfer coefficient that is greater than $h_{shalt}$, in particular with liquid materials and tissues of the human and animal body. Examples of such articles which come into contact with materials having a thermal transfer coefficient greater than $h_{schalt}$ are catheters, such as steerable or expandable catheters, vessel supports, such as self-expanding and/or removable vessel supports and/or stents, in particular for the coronary region, the bladder or the kidneys or vein filters, such as Vena-Cava filters.

The invention particularly also relates to articles according to the invention for application in a method for surgical or therapeutic treatment of the human or animal body in a diagnostic procedure, wherein the article is brought into contact with parts of a human or animal body. Examples of articles for application in a method for surgical or therapeutic treatment are, for example, drug delivery systems, in particular implantable and externally controllable drug delivery systems, medical devices, such as medical devices optimized for minimal invasive surgery, such as the guide wires, in particular steerable guide wires, or stitching materials.

The invention also relates to the use of the article according to the invention in the medical field, in particular the application in a method for surgical or therapeutic treatment of the human or animal body or in diagnostic procedures, wherein the article is brought into contact with parts of a human or animal body. Suitable uses for the article according to the invention are, for example, the creation of stimulatable knots, attachments or implants, or a surgery-free or post-operative change of implants, for example the adaptation with respect to position, size, function, flow-through or flow resistance. Later, i.e. postoperative, changes of the position are used, for example, for electrodes of heart pacemakers. Changes in the size in the context of the invention refer to a change of a geometric parameter, such as a change in the length, width, height, diameter or in the general shape. The application of the article according to the invention is of particular interest for implants or prostheses in the growth regions of the body, because with the article of the invention, for example, joint prostheses and/or bone replacement implants can be adapted to the growth of a human and/or an animal. Functional changes refer to, for example, unfolding a venous filter, such as for the Vena Cava or the expansion of vessel supports and/or stents. Even certain organ functions can be controlled with the article according to the invention, for example by a stimulatable adaptation of the blood supply. Moreover, the articles according to the invention are also suitable for calling up or retrieving one or more diagnostic functions of an implantable monitoring system. The aforementioned applications and possible uses only represent selected examples from the medical field, in particular from the field of regenerative medicine and are therefore not intended to be limiting. Additional suitable fields and possibilities for applications are known to a skilled artisan.

The invention also relates to a method for producing an article according to the invention having at least one switching segment, with the steps of:
a) preparing a shape memory compound of the at least one switching segment, which comprises at least one thermo-programmable shape memory polymer and particles incorporated therein, which particles are suitable to be heated up in an alternating electromagnetic field, wherein the shape memory compound has a thermal transfer coefficient $h_{schalt}$, and
b) depositing on the shape memory compound of the at least one switching segment an isolating region which has a thermal transfer coefficient $h_{iso} < h_{schalt}$, so that the isolating region surrounds the shape memory compound, and
wherein step b) is carried out concurrent with step a) or subsequent to step a).

The shape memory compound can basically be produced with methods and technologies known to the skilled artisan, for example by forming from the polymer melt, continuous and/or discontinuous single-layer or multilayer extrusion processes, continuous and/or discontinuous single-layer or multilayer injection molding processes or with a joining process, whereby several prefabricated parts are connected with each other. In particular, DE 10 2007 061 342.5 describes in detail suitable shape memory polymers with embedded particles which are adapted to heat up in an alternating electromagnetic field, as well as method for producing such polymers and methods for producing shape memory compounds that contain such polymers. Preferably, the shape memory compound of the at least one switching segment is produced by deformation from a polymer melt, by a continuous and/or discontinuous, single-layer and/or multilayer extrusion or injection molding process, and/or by a joining process of several prefabricated elements.

The isolating region can be deposited on the shape memory compound of a switching segment by using several fabrication methods known to the skilled artisan from other contexts. Particularly suitable are foaming processes, layering processes (for example airbrush processes) or phase inversion processes. In the foaming process, gas (preferably carbon dioxide) is introduced into the polymer melt in a supercritical state at high pressure and high temperature and maintained in equilibrium under these conditions. After the temperature and/or the pressure is lowered, spontaneous relaxation and the foaming process take place, with the result that porous morphologies are created in the shape body. This "foaming" can be implemented in a discontinuous process (pressure quench) either continuously during the extrusion or thereafter. Complete foaming of the shape memory compound is achieved as soon as the equilibrium state has been established over the entire body to be foamed. The process can be terminated prematurely by relieving the gas pressure, thereby attaining partial foaming. With increasing duration of the foaming process, an article according to the invention is isolated from the outside inwards until complete encasement is reached.

Porous structures can also be produced with phase inversion processes. The liquid phase of a polymer (polymer solution or polymers melt) is hereby subjected to a phase inversion caused by cooling of the polymers liquid or by introducing a nonsolvent.

Alternatively, layers of the isolating region may be deposited on the corresponding locations of the shape memory compound, for example by spraying (optionally by using an airbrushing method).

Preferably, the isolating region is deposited by foaming, spraying and/or phase inversion; in particular, the isolating region can be produced by foaming and/or phase inversion of the at least one thermo-programmable shape memory polymer of the shape memory compound. In a particularly preferred embodiment, the isolating region is produced by foaming and/or phase inversion of one or more materials which are different from the at least one thermo-programmable shape memory polymer of the shape memory compound.

For example, the solution according to the invention encompasses the following types of processes:
i) The solution according to the invention can be attained in that the shape memory compound consists only of a single material.
ii) The solution according to the invention can be attained in that the shape memory compound is made from several different materials, in particular from two different materials, wherein at least one material represents a thermo-programmable shape memory polymers.
iii) The solution according to the invention can be attained in that the shape memory compound is produced by continuous extrusion and an integral nonuniform morphology across the cross-section is attained through simultaneous partial foaming of the materials.
iv) The solution according to the invention can be attained in that the shape memory compound is produced by extrusion and an integral nonuniform morphology across the cross-section is attained in a subsequent "pressure quench" process through partial foaming of the materials.
v) The solution according to the invention can be attained in that the shape memory compound is produced by extrusion and an integral nonuniform morphology across the cross-section is attained through a subsequent partial phase inversion process of the materials.
vi) The solution according to the invention can be attained in that the shape memory compound is produced by continuous multilayer extrusion and an integral nonuniform morphology across the cross-section is attained through partial foaming of the materials.
vii) The solution according to the invention can be attained in that the shape memory compound is produced by multilayer extrusion and an integral nonuniform morphology across the cross-section is attained in a subsequent "pressure quench" process through partial foaming of the materials.
viii) The solution according to the invention can be attained in that the shape memory compound is produced by multilayer extrusion and an integral nonuniform morphology across the cross-section is attained in a subsequent partial phase inversion process of the materials.
ix) The solution according to the invention can be attained in that the shape memory compound is produced with a joining process and an integral nonuniform morphology across the cross-section is attained in a subsequent "pressure quench" process through partial foaming.

x) The solution according to the invention can be attained in that the shape memory compound is produced with a joining process and an integral nonuniform morphology across the cross-section is attained in a subsequent partial phase inversion process.

With the method of the invention, the isolating region can be created by foaming and/or phase inversion of a shape memory polymer of the shape memory compound.

With the method of the invention, the isolating region can also be produced, for example, by foaming and/or phase inversion of one or more materials which are different from the shape memory polymer of the shape memory compound.

To better illustrate this specially structured material, an example of an exemplary morphological structure is shown in FIG. 3.

The invention also relates to an article made from a shape memory compound, which includes a shape memory polymer with a hard domain and at least one switching domain, as well as particles incorporated in the shape memory polymer, which are adapted to heat up in an alternating electromagnetic field, characterized in that the article has a structure such that an exterior region of the body in cross-section has smaller thermal transfer coefficients than an interior region in cross-section. In particular, the exterior region can have a structure causing the smaller thermal transfer coefficients, in particular a foam structure. Preferably, the exterior region may have a material with a specific (mass-related) thermal transfer coefficient that is smaller than the specific thermal transfer coefficient of the material of the interior region.

The present invention also relates to a method for producing a shape memory compound according to the invention, wherein a shape mass, which includes a shape memory polymer with a hard domain and at least one switching domain, as well as particles embedded in the shape memory polymer, which are adapted to heat up in an alternating electromagnetic field, is mixed with a propellant and partially foamed in an injection molding process.

BRIEF DESCRIPTION OF THE DRAWINGS

Exemplary embodiments of the invention will now be described with reference to the appended drawings. These show in:

FIGS. 3 a)-e) Morphological structure of an embodiment of a shape memory compound according to the invention with a specially structured layer structure;

DETAILED DESCRIPTION OF THE PRESENTLY PREFERRED EMBODIMENTS

Exemplary Embodiments

Example 1

A shape memory polymer containing nanoparticles (Mag-Silica 50-85) is deformed by an injection molding process into a cylinder having a diameter of 5 mm and a height of 5 mm. The cylinder is partially foamed in a subsequent process step in an autoclave. The porosity in the outer cylinder layer is hereby increased due to the contact between the polymer material and carbon dioxide (supercritical) at elevated pressure (100 bar) and high-temperature (100° C.). After 5 minutes (saturation phase), the pressure is spontaneously decreased at a rate of 900 bar/min and the sample is cooled down (room temperature) in the autoclave. The produced foamed isolating region has an average layer thickness of about 0.4 mm.

Figure 7:
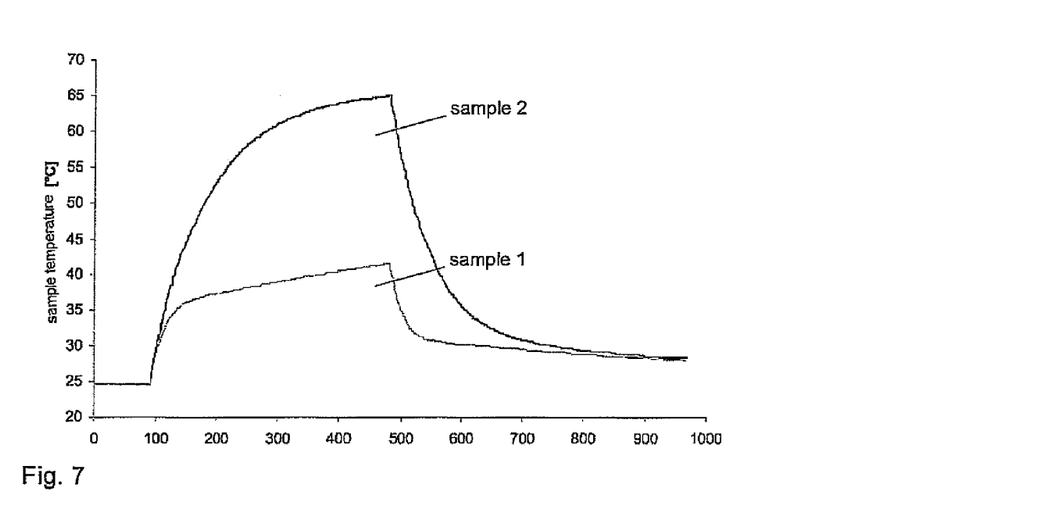
FIG. 7 A temperature curve off differently structured shape memory compounds in the EMF in different media (water, air)

A polymer cylinder (sample 1) which is not subjected to this second process step and a polymer cylinder with a porous outer isolating region (sample 2) which is subjected to the second process step are the starting point of this exemplary embodiment. In both samples, the temperature in the interior of the sample body can be measured with a thermocouple. The starting sample (sample 1) and the sample 2 which corresponds to the method according to the invention are exposed to an alternating EMF at a frequency of 253 kHz and a field strength of 12.6 kA/m. After 380 seconds the temperature increase is measured in each of the test samples, which were placed in water (high thermal transfer coefficient). Sample 1 had an internal temperature of 42° C., whereas the sample to according to the invention had a temperature of 65° C. FIG. 7 illustrates the effect according to the invention.

Under analogous conditions, a significantly higher temperature can be produced with solutions according to the invention—in particular in surrounding media having high thermal transfer coefficients.

Example 2

A polymer test sample was produced from the shape memory polymer poly-(etherurethane) with 5 mass-% Inc. nanoparticles (iron oxide). The test sample was transferred to a foaming process in supercritical $CO_2$, wherein an isolating region with a foam structure is created in cross-section of the test sample (see FIGS. 3 a) to d)). The isolating region with uniform structure has in cross-section of the test sample a thickness of about 0.4 mm and is located at the outermost surface of the cylinder. The diameter of the foam cells is in a range from 5 to 50 μm and depends on the distance from the cell to the surface of the test sample. The closer the form is to the surface of the test sample, the smaller is its diameter, and vice versa. The pore size of the foam structure in the isolating region of the test sample can be controlled through control of the pressure reducing step. FIG. 3b) shows that the nanoparticles, in this case iron oxide particles, are well distributed in the polymer matrix. It should be particularly noted that the isolating region has a smooth outermost surface (see FIGS. 3 a) to c)). The smooth fluid-impermeable surface of the isolating region has the function to ensure mechanical stability of the body and to prevent other materials, such as liquids or gases, from entering the interior of the body. It is the function of the isolating region of the test sample to reduce heat transfer of the test sample in the marginal region, whereas in a shape memory compound the test sample can be heated in an electromagnetic field via the embedded nanoparticles without causing significant heat dissipation into the surroundings of the test sample.

Figure 4:
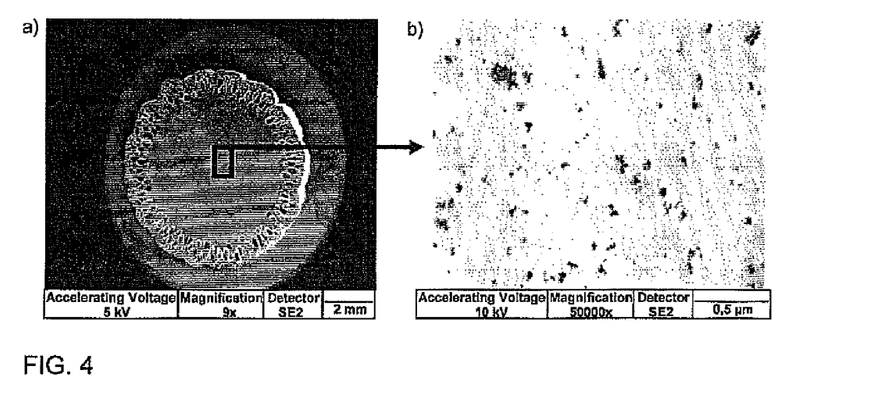
FIG. 4 A cylindrical embodiment of an article (a) according to the invention with an enlarged detail of the core region (c)

To demonstrate the efficiency of the foamed isolating region as an insulator, a polymer cylinder was prepared (poly (etherurethane) with 5 mass-%) nanoparticles, which had a diameter of $D_{iso+schalt}$ of 7 mm and an isolating region having a shape memory compound with a diameter of $D_{schalt}$ off 6 mm and a length of 12 mm (FIG. 4 a)). FIG. 4 b) shows an enlarged detail of the core region of the poly (etherurethane) matrix, wherein the black regions represent the nanoparticles-sized iron oxide particles.

Figure 5:
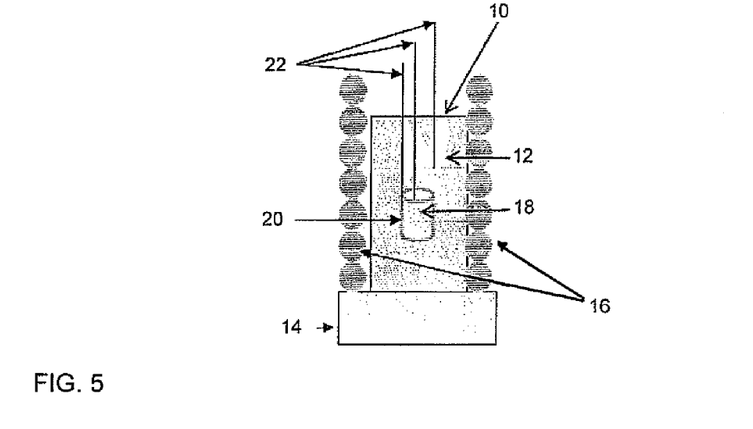
FIG. 5 A schematic test setup for determining the temperature behavior of different samples in an alternating magnetic field in a medium with a high thermal transfer coefficient.
Figure 6:
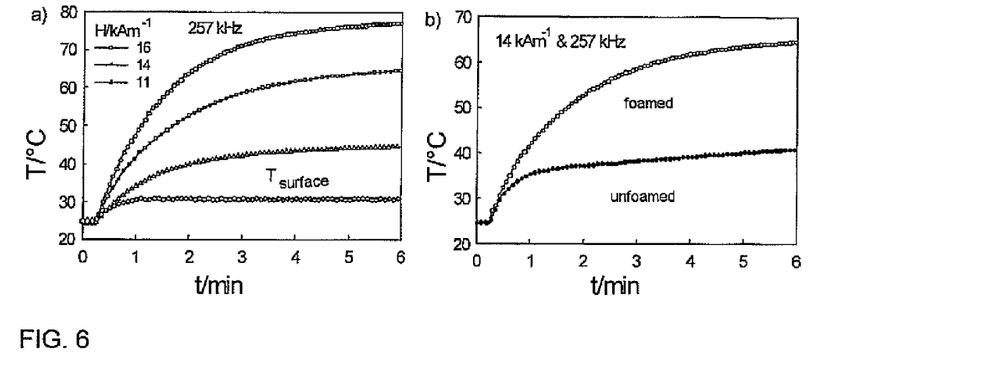
FIG. 6 A temperature curve of a) a polymer cylinder in water with a foamed isolating region with EMF of different field strength, and of b) a comparison between a polymer cylinder with or without a foamed isolating region.

According to FIG. 5, the cylindrical sample was transferred to a glass container 10 (diameter 25 mm, height 55 mm) which was filled with distilled water 12. The glass container 10 is positioned on an insulating plastic support 14 and a surrounded by coils 16 of an inductor. The inductor itself is not shown. The temperature in the sample 18, in the foam sheath 20 and in the surrounding water 12 was determined with different temperature sensors 22. FIG. 5 shows a schematic diagram the test apparatus. The arrangement was subjected to an alternating electromagnetic field having a frequency off 257 kHz and different field strength. As shown in FIG. 6 a), the cylinder 18 could be heated with increasing field strength faster and overall to a higher maximum temperature. The temperature at the surface of the foamed cylinder remained essentially constant at 30° C. In addition, essentially no temperature change in the water surrounding the cylinder could be detected.

Subsequently, the temperature change in a cylinder with a foamed isolating region was measured at a constant field having a frequency of 257 kHz and a field strength of 14 kA/m and compared with the temperature curve of the cylinder of identical structure which was not subjected to the foaming process and therefore does not have a corresponding isolating region according to the invention. As seen in FIG. 6b), the temperature in the cylinder with isolating region increases much faster and also reaches a higher maximum value than in the comparison cylinder.

Example 3

Figure 8:
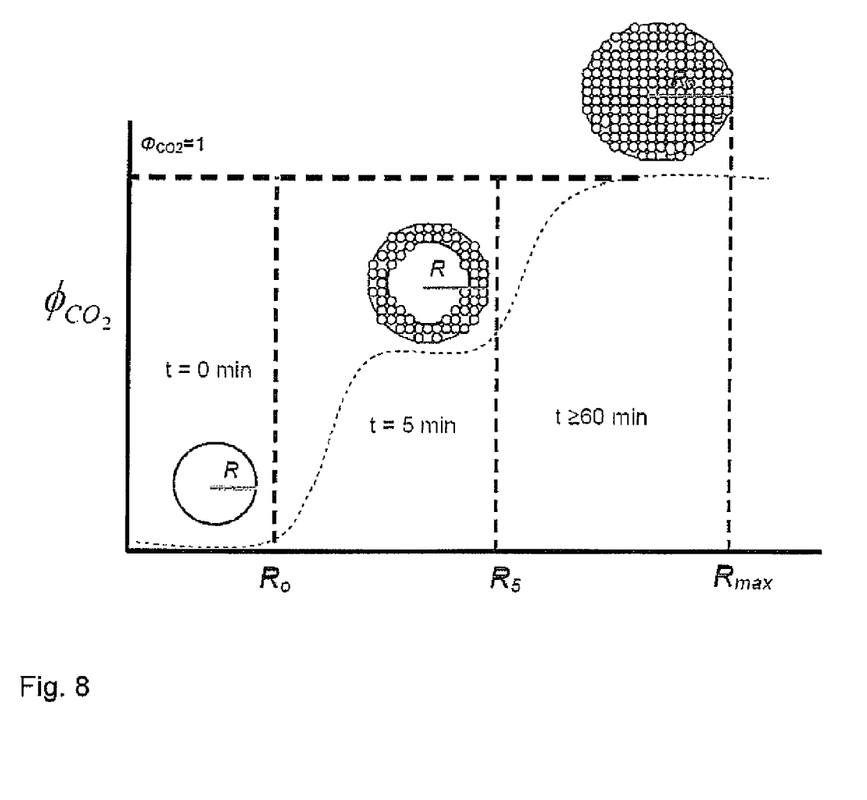
FIG. 8 A diagram for illustrating the foaming process.

The foaming process of a spherical body with the radius R is schematically illustrated in FIG. 8. Plotted is the fraction $\Phi$ of $CO_2$ in equilibrium as a function of the radius R. At t=0 min the entire body is not yet a foamed. At $\Phi(CO_2)=1$, an equilibrium has been established across the entire radius R, wherein the equilibrium is established from the outside inwardly. After relaxation, the body then has a complete foam structure. The complete equilibrium $\Phi(CO_2)=1$ is reached after 60 min. Before the equilibrium is established across the entire body, the foaming process can be terminated at any time, for example after 5 min, through relaxation. After 5 min, equilibrium has already been achieved across a certain portion of the radius, here $R_5$. After relaxation, this region of $R_5$ has the insulating foam structure. Partial foaming can thus be achieved by suitable process control and with timely termination of the foaming process.

Example 4

Figure 9:
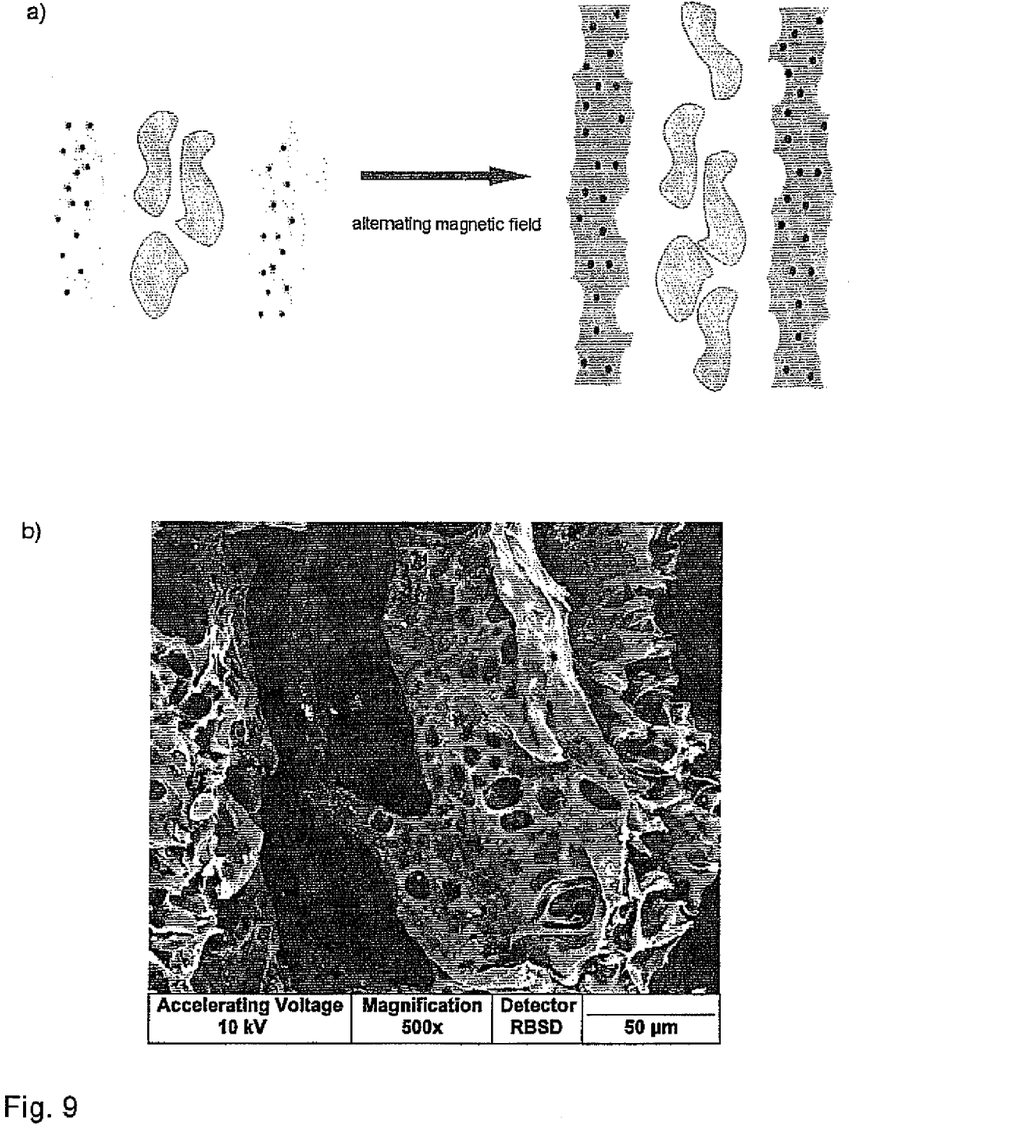
FIG. 9 A schematic illustration of an expansion of an artificial blood vessel from a shape memory compound according to the invention (a), and an electron micrograph of such vessel in the longitudinal direction (b)

A shape memory compound according to the invention is used as vessel replacement for producing artificial blood vessels. Under the influence of the alternating magnetic field, a shape change in form of an expansion of the artificial vessel walls in the longitudinal direction is produced. FIG. 9a) shows schematically this transition. Advantageously, a short vessel replacement piece can be inserted in this way with minimal damage to the natural vessel and subsequently expanded to the desired length. The vessel wall is hereby stabilized beyond the location of the surgery, which is advantageous for the healing process. FIG. 9b) shows the pore structure used for the artificial blood vessel. The channel forming the artificial blood vessel can be seen in a black.

Figure 10:
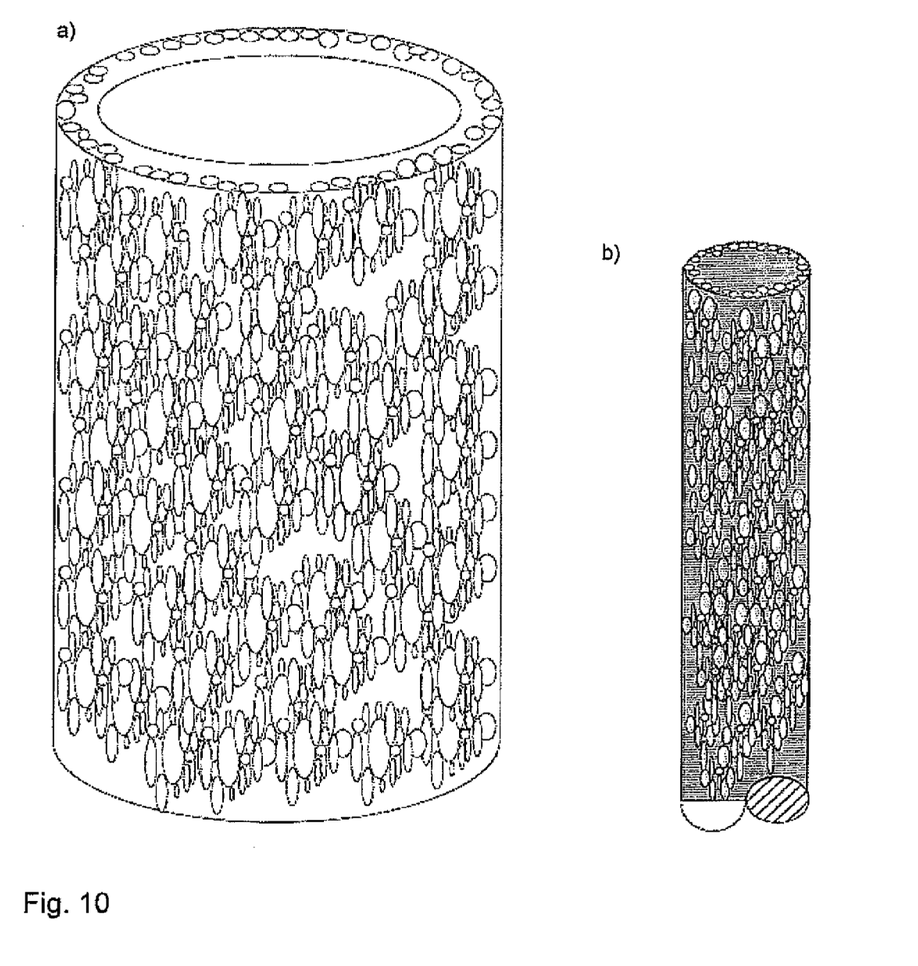
FIG. 10 A schematic illustration of foaming of an article according to the invention with tubular (a) and cylindrical (b) geometry.

FIG. 10 shows schematically foaming of different geometric bodies for medical use. A tubular geometry, as used with catheters and vessel replacement, is selectively foamed on the sheath surface (FIG. 10 a)). Solid cylindrical bodies are used, for example, in form of mono-filaments as stitching material. Such foamed mono-filament is schematically illustrated in FIG. 10b).

| List of references symbols | |
| --- | --- |
| 10 | Glass container |
| 12 | Distilled water |
| 14 | Plastic support |
| 16 | Coils of an inductor |
| 18 | Sample |
| 20 | Foam sheath |
| 22 | Temperature sensor |

The invention claimed is:

1. An article with at least one switching segment, wherein the at least one switching segment comprises
   a) a shape-memory compound comprising at least one thermo-programmable shape memory polymer and particles embedded therein, which particles are suitable to heat up in an alternating electromagnetic field, wherein the shape memory compound has a thermal transfer coefficient $h_{schalt}$;
   b) an isolating region surrounding the shape memory compound a) and having a thermal transfer coefficient $h_{iso}$; wherein $h_{iso} < h_{schalt}$.

2. The article according to claim 1, wherein the ratio $h_{iso}/h_{schalt}$ is ≤0.9.

3. The article according to claim 1, wherein the isolating region has substantially no particles which are suitable to heat up in an alternating electromagnetic field.

4. The article according to claim 1, wherein the isolating region comprises a material or is made of a material with a specific thermal conductivity $\lambda_{iso}$, which is smaller than the specific thermal conductivity $\lambda_{schalt}$ of the at least one thermo-programmable shape memory polymer of the shape memory compound.

5. The article according to claim 1, wherein the isolating region has a structure which is different from the structure of the shape memory compound.

6. The article according to claim 1, wherein the isolating region has a foam structure.

7. The article according to claim 1, wherein the material of the isolating region comprises a gas.

8. The article according to claim 1, wherein the ratio of the average diameter of the isolating region and the shape memory compound ($D_{iso+schalt}$) to the average diameter of the shape memory compound ($D_{schalt}$) is selected in cross-section of the at least one switching segment ($D_{iso+schalt}/D_{schalt}$ such that a switching temperature of the at least one shape memory polymer of the shape memory compound can be attained in the shape memory compound through excitation with an alternating electromagnetic field, wherein the at least one switching segment is in an environment having a thermal transfer coefficient which is greater than the thermal transfer coefficient of the shape memory compound of the switching segment.

9. The article according to claim 8, wherein the diameter ratio $D_{iso+schalt}/D_{schalt}$ is selected such that the at least one switching segment attains the switching temperature in an environment of water and/or in an alternating electromagnetic field having a frequency of 245 to 265 kHz and a field strength of 10 to 16 kA/m.

10. The article according to claim 8, wherein the ratio of the average diameter of the isolating region and of the shape memory compound to the average diameter of the shape memory compound in cross-section of the at least one switching segment is $D_{iso+schalt}/D_{schalt} \geq 1.01$.

11. The article according to claim 1, wherein the isolating region comprises pores, which are distributed over the cross-section of the isolating region along a pore size gradient, wherein the pores in an outer region of the isolating region are on average smaller than the pores in an inner region of the isolating region.

12. A method for producing an article with at least one switching segment according to claim 1, comprising the steps of:
a) preparing a shape memory compound of the at least one switching segment, which comprises at least one thermo-programmable shape memory polymer and particles incorporated therein, which particles are suitable to be heated up in an alternating electromagnetic field, wherein the shape memory compound has a thermal transfer coefficient $h_{schalt}$; and
b) depositing on the shape memory compound of the at least one switching segment an isolating region which has a thermal transfer coefficient $h_{iso} < h_{schalt}$, so that the isolating region surrounds the shape memory compound, and
wherein step b) is carried out concurrent with step a) or subsequent to step a).

13. The method according to claim 12 wherein the shape memory compound of the at least one switching segment is produced by deformation from a polymer melt, by a continuous and/or discontinuous, single-layer and/or multilayer extrusion or injection molding process and/or by a joining process of several prefabricated elements.

14. The method according to claim 12, wherein the isolating region is deposited by foaming, by spraying and/or by phase inversion.

15. The method according to claim 12, wherein the isolating region is produced by foaming and/or phase inversion of the at least one thermo-programmable shape memory polymer of the shape memory compound.

16. The method according to claim 12, wherein the isolating region is produced by foaming and/or phase inversion of one or more materials, which are different from the at least one thermo-programmable shape memory polymer of the shape memory compound.

17. The article according to claim 1, wherein the article is in contact with a material having a thermal transfer coefficient greater than $h_{schalt}$.

18. The article according to claim 17 wherein the material is a liquid or tissue of a human or animal.

19. The article according to claim 2 wherein the ratio $h_{iso}/h_{schalt}$ is $\leq 0.1$.

20. The article according to claim 2 wherein the gas is $CO_2$ or air.

* * * * *